United States Patent [19]

Schlossman

[11] Patent Number: 4,591,502

[45] Date of Patent: May 27, 1986

[54] COMPRESSING AID FOR COSMETIC POWDERS

[76] Inventor: Mitchell L. Schlossman, 20 Lake Shore Dr., Rockaway, N.J. 07866

[21] Appl. No.: 444,451

[22] Filed: Nov. 24, 1982

[51] Int. Cl.$^4$ .......................... A61K 7/021; C08J 3/02
[52] U.S. Cl. .......................................... 424/63; 424/69; 106/271; 514/772; 514/844
[58] Field of Search ..................... 424/69, 63, DIG. 5; 156/283, 334; 106/271, 308 F

[56] References Cited

U.S. PATENT DOCUMENTS

| | | | |
|---|---|---|---|
| 1,996,168 | 4/1935 | Ornfeldt | 424/69 |
| 3,117,101 | 1/1964 | Moyer | 156/334 |
| 3,800,034 | 3/1974 | Kircher et al. | 424/63 |
| 3,847,622 | 11/1974 | Brandl et al. | 106/271 X |
| 3,911,105 | 10/1975 | Papantoniou et al. | 424/63 |
| 3,978,207 | 8/1976 | Fotiu et al. | 424/63 |
| 4,049,792 | 9/1977 | Elsnau | 424/66 |
| 4,106,932 | 8/1978 | Blachford | 75/252 |
| 4,279,890 | 7/1981 | Harris et al. | 424/69 |
| 4,305,931 | 12/1981 | Kawano et al. | 424/69 |
| 4,362,642 | 12/1982 | Carter et al. | 252/135 X |
| 4,404,035 | 9/1983 | Ona et al. | 106/271 |

FOREIGN PATENT DOCUMENTS

| | | | |
|---|---|---|---|
| 0028906 | 2/1980 | Japan | 424/63 |
| 0136213 | 10/1980 | Japan | 424/63 |
| 1128312 | 9/1968 | United Kingdom | 424/63 |

OTHER PUBLICATIONS

The Encyclopedia of Polymer Science and Technology, vol. 14, pp. 768-779.

*Primary Examiner*—Esther M. Kepplinger
*Assistant Examiner*—Shawn P. Foley
*Attorney, Agent, or Firm*—Handal & Morofsky

[57] ABSTRACT

The compressing aid consists of particles of a synthetic saturated hydrocarbon wax having an average molecular formula of $C_{48}H_{98}$, an average molecular mass of about 700, a minimum congealing point of about 204° F. and an average particle size of about 10 microns. For greater ease in dispersion during blending of ingredients, the wax particles may be coated with 0.1 to 1.0% by weight of a lubricant such as dimethyl polysiloxane and low viscosity esters of $C_{10}$ to $C_{18}$ fatty acids or alcohols such as isopropyl myristate, lauryl lactate and ethylhexyl palmitate.

6 Claims, No Drawings

COMPRESSING AID FOR COSMETIC POWDERS

BACKGROUND OF THE INVENTION

Cosmetic powders are currently available in loose and pressed form. The majority of these powders, face powder, blusher, eyeshadow etc., are used in pressed form. This form of the product is very practical since it is easy to carry along and can be used whenever needed for touching-up.

The main properties of a pressed powder are: easy powder release without dustiness, good skin adhesion, and a strong cake which does not crumble, break or cake-up.

In order to achieve all of these characteristics, the present pressed powder formulations contain a blend of several ingredients, each chosen for their specific quality.

The major constituents of a regular shaded pressed powder are talc and color; all other ingredients being used to achieve compressibility. Binding is a special property inherent to a pressed powder formulation. Most powder constituents found in formulations are not "binding" in themselves and therefore other agents such as metallic stearates, kaolin, and fatty materials are used as additives to insure proper adhesion and compressibility. Fatty materials, such as mineral oil or fatty alcohols, are used in liquid form to aid in binding, improve skin adhesion and reduce cake dustiness.

In frosted products, mica and titanium dioxide coated mica (pearlescent materials) are the major powder constituents. In order to compress these materials, a large portion of about 20–40 percent of the composition is additives. Such large amounts of non-pearlescent ingredients reduce the "frosty" effect of the product.

In U.S. Pat. No. 1,996,168, 1 to 5% of beeswax or synthetic wax and a small amount of soap are combined in melted form with mineral oil and heated. After cooling the mixture, powdery materials such as talc are added. No mention is made of compressing this powdery product. In U.S. Pat. No. 1,707,684, olive oil is used as a waterproof binder for powder in loose form.

U.S. Pat. No. 3,300,387 discloses a pressed powder consisting of an anti-perspirant coated with 5–15% of a water-soluble wax-like material such as PEG and its methoxy derivatives mixed with a powder base and an oily binder such as mineral oil, lanolin, vegetable oils and isopropyl esters of fatty acids.

The pressed powders of U.S. Pat. No. 3,800,034 contain binders such as gums, cellulose derivatives, gelatin, lignin, PVP, PVA and a complex magnesium silicate and lubricants such as metal stearates, liquid paraffin, fatty alchols, fatty acids and oils. U.S. Pat. No. 4,279,890 also employs metal stearates as binder and lubricant in pressed powders. Prevention of cracking in pressed powders was provided in U.S. Pat. No. 4,305,931 by incorporating a hydroxypropyl-etherified glycolipid ester.

Manufacturing of a pressed powder is long and tedious. It involves blending of all dry powder ingredients, wetting the blend with the liquid fatty material with subsequent balling up of the powder. In order to break up the powder balls and to achieve a uniform liquid distribution within the powder, it must then go through a micropulverization process. The inability to hold a shape after compression may vary with the chemical origin of the binding agent and the percentage utilized in the pressed powder formulation.

SUMMARY OF THE INVENTION

The present invention relates to cosmetic compositions and particularly relates to a compressing aid for cosmetic pressed powders.

It is accordingly an object of the present invention to eliminate the addition of a large concentration of additives to pressed powders.

It is another object of this invention to increase the pearlescent effect of the product by reducing the concentration of additives.

It is another object of this invention to eliminate the addition of a liquid binding agent. This eliminates the need for adjusting wetting agents for oil absorption of pigment concentration.

It is a further object of this invention to drastically reduce the processing time required of pressed powders; effecting cost savings.

It is still another object of the present invention to provide pressed powders which have good compressibility, low dusting, sufficient powder release without glazing, good skin adhesion, smooth surface, and a strong cake without crumbling, therefore improving shipping qualities.

In accordance with the present invention, it has been found that when a synthetically prepared, saturated hydrocarbon wax, either alone or treated with a lubricant such as a low viscosity fatty ester or silicone fluid, can act as a compressing aid for pressed powders to attain the above-mentioned objects.

DETAILED DESCRIPTION

The synthetically prepared saturated hydrocarbon wax is in powder form with an average particle size of about 10 microns. As stated, the wax itself can act as a compressing aid, but it is difficult to disperse uniformly in small concentrations within the powder because of its tackiness. Coating the surface of the wax with about 0.1 to 1.0% of a fatty ester or silicone fluid lubricates the fine wax particles and aids in its dispersion.

The saturated hydrocarbon wax has formula $C_nH_{2n+2}$ with average molecular formula of $C_{48}H_{98}$ and average molecular mass of 700. It is a hard, brittle, high melting wax powder, with a congealing point of 204° F. minimum, commercially available under various trade names.

The small particles of the compressing aid impart compressibility to noncompressing systems even when present in concentrations of 10 percent or less by weight.

The esters used to coat the wax are low viscosity esters of fatty acids or alcohols having 10 to 18, preferably 12 to 16, carbon atoms. Examples of such esters are isopropyl myristate, lauryl lactate and ethylhexyl palmitate.

The silicone fluid is dimethyl polysiloxane, a water immiscible silcone oil consisting of dimethylsiloxane polymers. CTFA name: Dimethicone.

Treatment of the wax particles with the ester or silicone is carried out in a high speed blender, such as a "Munson Rotary Batch Mixer" or a "Baker Perkins Drydispenser", by spraying the liquid into the powder in the blender.

The above coating on the wax is not needed if the wax is predispersed in a base, such as mica, talc, etc.

The following are examples of typical formulations using the compressing aid according to the invention for cosmetic pressed powders.

EXAMPLE I

| Ingredients | w/w % |
| --- | --- |
| Pearly Material *(colored) | 90.00 |
| Compressing Aid (uncoated wax) | 10.00 |
| | 100.00 |

*Presperse Colors sold by Presperse Inc., South Plainfield, New Jersey.

EXAMPLE II

| | |
| --- | --- |
| Talc | 90.00 |
| Iron Oxide pigments | 4.00 |
| D & C Organic Lakes | 1.00 |
| Compressing Aid (ester coated wax) | 5.00 |
| | 100.00 |

EXAMPLE III

| | |
| --- | --- |
| Mica Classified Particle Size | 85.00 |
| Iron Oxide Pigments | 5.00 |
| Compressing Aid (silicone coated wax) | 10.00 |
| | 100.00 |

The manufacturing of the pressed powders according to the invention is very simple and involves blending the compressing aid with the pigments, mica talc, etc., and compressing the mixture into godets. Micropulverization is only needed if the pigment particle size needs to be reduced.

A comparison was made of pressed powders according to the invention with two similar pressed powders currently on the market. The following table shows the advantages of the invention, especially in the frost composition. The tests were run with two products of the cream shade type and two of the frost type in accordance with the invention. One of each type incorporated the uncoated synthetic wax as compressing aid and the other of each type incorporated the coated wax as compressing aid. Although the coated wax blended more easily with the other ingredients, the properties of the final product were the same. The cream shade base consisted of talc and iron oxide and the frost base consisted of titanium dioxide and mica.

| | Pressed Powders | | | |
| --- | --- | --- | --- | --- |
| | Currently on the market | | Made with compressing aid | |
| Properties: | Cream Shade | Frost | Cream shade | Frost |
| Compressibility | good | poor | good | good |
| Powder Release | good | too much | good | good |
| Glaze | yes | no | no | no |
| Dustiness | no | yes | no | no |
| Skin adhesion | good | poor | good | good |
| Wear | good | fair | good | good |
| Crumbling | no | yes | no | no |

I claim:

1. A compressing aid for cosmetic pressed powders, said aid consisting essentially of particles of a synthetic saturated hydrocarbon wax having an average molecular formula of $C_{48}H_{98}$, an average molecular mass of about 700, a minimum congealing point of about 204° F., and an average particle size of about 10 microns, said wax particles being coated with an amount of lubricant equal to from about 0.1 to 1.0% of the weight of said wax, said lubricant selected from the group consisting of dimethyl polysiloxane, isopropyl myristate, lauryl lactate and ethylhexyl palmitate.

2. In a cosmetic pressed powder comprising a powder component, a pigment component and a compressing aid, the improvement which comprises a compressing aid consisting essentially of particles of a synthetic saturated hydrocarbon wax having an average molecular formula of $C_{48}H_{98}$, an average molecular mass of about 700, a minimum congealing point of about 204° F. and an average particle size of about 10 microns, and wherein the amount of said wax used is effective to impart compressibility and adhesion to the powder.

3. The pressed powder of claim 2, wherein the compressing aid is used in the amount of about 5 to 10% by weight based on the total weight of the pressed powder.

4. The compressed powder of claim 2, wherein said wax particles are coated with an amount of lubricant equal to from about 0.1 to 1.0% of the weight of said wax, said lubricant selected from the group consisting of dimethyl polysiloxane, isopropyl myristate, lauryl lactate and ethylhexyl palmitate.

5. The pressed powder of claim 2 wherein the powder component is at least one selected from the group consisting of talc, mica, and titanium dioxide coated mica and the pigment component is at least one selected from the group consisting of iron oxide pigments and organic lakes.

6. The pressed powder of claim 4, wherein the powder component is at least one selected from the group consisting of talc, mica and titanium dioxide coated mica and the pigment component is at least one selected from the group consisting of iron oxide pigments and organic lakes.

* * * * *